United States Patent [19]

Sarantakis et al.

[11] Patent Number: 5,336,677
[45] Date of Patent: Aug. 9, 1994

[54] SUBSTITUTED AMINOPYRIMIDINES AS ANTIHYPERTENSIVES

[75] Inventors: Dimitri Sarantakis, Newtown, Pa.; James J. Bicksler, Cranbury, N.J.; John W. Ellingboe, Princeton, N.J.; Madelene Nikaido, Plainsboro, N.J.

[73] Assignee: American Home Products Corporation, Madison, N.J.

[21] Appl. No.: 900,639

[22] Filed: Jun. 18, 1992

Related U.S. Application Data

[63] Continuation-in-part of Ser. No. 782,026, Oct. 24, 1991, abandoned.

[51] Int. Cl.$^5$ .................. A61K 31/505; C07D 239/42
[52] U.S. Cl. .................................... 514/256; 544/296; 544/298; 544/319; 544/326; 544/327; 544/328; 544/329; 544/253; 514/269; 514/258
[58] Field of Search ............... 544/298, 319, 296, 326, 544/327, 328, 329, 253; 514/256, 258, 269

[56] References Cited

FOREIGN PATENT DOCUMENTS 2027339 4/1991 Canada .
0419048 7/1990 European Pat. Off. .
0475206 3/1992 European Pat. Off. .

*Primary Examiner*—John M. Ford
*Attorney, Agent, or Firm*—Walter Patton; R. F. Boswell, Jr.

[57] ABSTRACT

This invention relates to substituted 4-aminopyrimidines, which by virtue of their ability to antagonize angiotensin II are useful for the treatment of hypertension, congestive heart failure, and restenosis. The compounds are also useful for reducing lipid levels in the blood plasma and are thus useful for treating hyperlipidemia and hypercholesterolemia. Also disclosed are processes for the production of said compounds and pharmaceutical compositions containing said compounds.

27 Claims, No Drawings

SUBSTITUTED AMINOPYRIMIDINES AS ANTIHYPERTENSIVES

This is a continuation-in-part application of copending application Ser. No. 07/782,026, filed Oct. 24, 1991, now abandoned.

BACKGROUND OF THE INVENTION

This invention relates to substituted aminopyrimidines which are useful for the treatment of hypertension and congestive heart failure. The compounds of this invention are also useful as lipid lowering agents.

The compounds of this invention achieve their hemodynamic effects by antagonizing the effects of angiotensin II; the active component of the renin angiotensin system. Angiotensinogen is converted to angiotensin I by the action of the enzyme renin. Angiotensin II (A II) is formed by angiotensin converting enzyme (ACE) acting on angiotensin I. A II is a powerful vasoconstrictor and is implicated as the cause of high blood pressure in a number of species including man. A II elicits these vasopressor responses by acting at specific receptor sites. The compounds of this invention compete with A II for these receptor sites, thus antagonizing the vasopressor effects of A II.

E. E. Allen et al. disclose N-substituted oxopyrimidines in EP 0419048 A. E. E. Allen et al. describe 4-oxoquinazolines in EP 0411766 A. D. A. Roberts et al. describe quinoline ethers in EP 0412848 A. D. J. Carini et al. in U.S. Pat. No. 4,880,804 describe N-substituted benzimidazoles. P. Chakravarty et al. disclose similar imidazole structures in EP 0401030 A where the phenyl aromatic ring is replaced by a seven membered heterocycle. Azabenzimidazoles are described by P. Herold et al. in EP 0415886 A. D. J. Carini et al. disclose N-substituted imidazoles in EP 0253310, EP 0324377, and U.S. Pat. No. 4,916,129. D. J. Carini et al. disclose N-substituted pyrazoles, pyrroles and triazoles in EP 0323841. Similar pyrazole derivatives are disclosed by T. Naka et al. in EP 0411507 A and additional triazoles are described by L. L. Chang et al. in EP 0412594 A. All of the above are claimed as A II antagonists.

The compounds of this invention differ from the above mentioned prior art in that they contain a substituted 4-aminopyrimidine ring.

DESCRIPTION OF THE INVENTION

This invention relates to substituted aminopyrimidines of the general formula I:

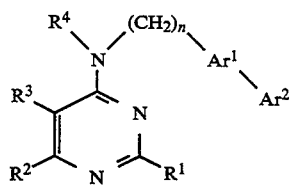

wherein
R$^1$ is alkyl of 1-6 carbon atoms, perfluoroalkyl of 1-6 carbon atoms, cycloalkyl of 3-7 carbon atoms, fluoro, chloro, or bromo;
R$^2$ is hydrogen, alkyl of 1-6 carbon atoms, perfluoroalkyl of 1-6 carbon atoms, trifluoromethylalkyl of 1-6 carbon atoms, cycloalkyl of 3-7 carbon atoms, alkoxy of 1-6 carbon atoms, hydroxy, fluoro, chloro, bromo, or cyano;
R$^3$ is hydrogen, perfluoroalkyl of 1-6 carbon atoms, trifluoromethylalkyl of 1-6 carbon atoms, alkyl of 1-6 carbon atoms, alkenyl of 3-5 carbon atoms, alkynyl of 3-5 carbon atoms, aryl of 6-10 carbon atoms; aryl of 6-10 carbon atoms substituted with fluorine, chlorine or bromine; aralkyl of 7-12 carbon atoms; aralkyl of 7-12 carbon atoms substituted with alkyl of 1-6 carbon atoms, fluorine, chlorine or bromine; alkoxy of 1-6 carbon atoms or alkyl of 1-6 carbon atoms, cycloalkyl of 3-7 carbon atoms, pyridylmethyl, thienylmethyl, fluoro, chloro, bromo, cyano, hydroxyalkyl of 1-6 carbon atoms, (CH$_2$)$_m$CO$_2$R$^5$, (CH$_2$)$_m$CONR$^5$R$^6$; or taken together with R$^2$ is a methylene chain of 2-3 carbon atoms;
m is 1 to 4;
n is 0 to 3;
R$^4$ is hydrogen, alkyl of 1-6 carbon atoms, aryl of 6-10 carbon atoms, aryl of 6-10 carbon atoms substituted with halogen, alkylcarbonyl of 1-6 carbon atoms, pyridyl, or pyrimidinyl;
R$^5$ and R$^6$ are H or alkyl of 1-6 carbon atoms;
Ar$^1$ is

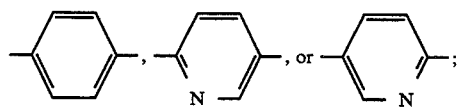

Ar$^2$ is

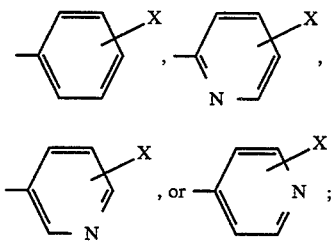

wherein X is

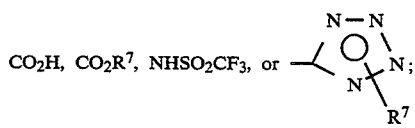

wherein R$^7$ is hydrogen, alkyl of 1-6 carbon atoms, benzyl, triphenylmethyl, or Sn(alkyl of 1-6 carbon atoms)$_3$;
and the pharmaceutically acceptable salts thereof.

A preferred aspect of the present invention is represented by general formula I:

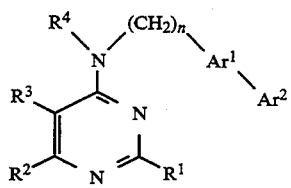

wherein
R¹ is alkyl of 1–6 carbon atoms, perfluoroalkyl of 1–6 carbon atoms, or cycloalkyl of 3–7 carbon atoms;
R² is hydrogen, alkyl of 1–6 carbon atoms, perfluoroalkyl of 1–6 carbon atoms, cycloalkyl of 3–7 carbon atoms, methoxy, hydroxy, chloro, or cyano;
R³ is hydrogen, trifluoromethyl, triflouormethylmethyl, trifluoromethylethyl, alkyl of 1–6 carbon atoms, allyl, alkynyl of 3–5 carbon atoms, phenyl, chlorophenyl, naphthyl, benzyl, benzyl substituted with chlorine or methyl, naphthylmethyl, cyclopropyl, cyclobutyl, cyclopentyl, cyclohexyl, pyridylmethyl, thienylmethyl, fluoro, chloro, cyano, hydroxyalkyl of 1–6 carbon atoms, $(CH_2)_mCO_2R^5$, $(CH_2)_mCONR^5R^6$; or taken together with R² is a methylene chain of 3 carbon atoms;
m is 1 to 4;
n is 0 to 3;
R⁴ is hydrogen, alkyl of 1–6 carbon atoms, phenyl, chlorophenyl, alkylcarbonyl of 1–6 carbon atoms, pyridyl;
R⁵ and R⁶ are H or alkyl of 1–6 carbon atoms;
Ar¹ is

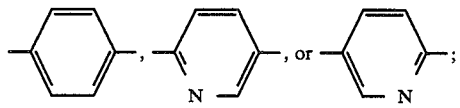

Ar² is

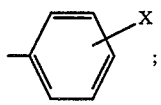

wherein X is $CO_2H$, $CO_2R^7$, $NHSO_2CF_3$, or

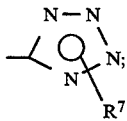

wherein R⁷ is hydrogen, alkyl of 1–6 carbon atoms, benzyl, triphenylmethyl, or Sn(alkyl of 1–16 carbon atoms)₃;
and the pharmaceutically acceptable salts thereof.
A more preferred aspect of the present invention is represented by general formula I:

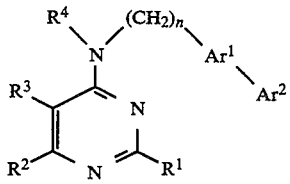

wherein
R¹ is methyl, ethyl, n-propyl, i-propyl, trifluoromethyl, pentafluoroethyl, cyclopropyl;
R² is hydrogen, methyl, ethyl, n-propyl, i-propyl, trifluoromethyl, pentafluoroethyl, cyclopropyl;
R³ is hydrogen, methyl, ethyl, n-propyl, i-propyl, n-hexyl, allyl, propargyl, p-chlorophenyl, benzyl, o-chlorobenzyl, 3-methylbenzyl, 2-naphthylmethyl, cyclopropyl, 2-thienylmethyl, hydroxyalkyl of 1–6 carbon atoms, $(CH_2)_mCO_2R^5$; or taken together with R² is a methylene chain of 3 carbon atoms;
m is 2;
n is 1;
R⁴ is hydrogen, acetyl, propionyl;
R⁵ is H;
Ar¹ is

Ar² is

wherein X is

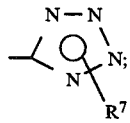

wherein R⁷ is hydrogen, t-butyl;
and the pharmaceutically acceptable salts thereof.
Specifically preferred compounds because of their antihypertensive activity are:
2,6-dimethyl-5-(2-propenyl)-N-[(2'-(1H-tetrazol-5-yl)[1,1-biphenyl]-4-yl)methyl]-4-pyrimidinamine and the pharmaceutically acceptable salts and solvates thereof;
6-methyl-5-(2-propenyl)-N-[(2'-(1H-tetrazol-5-yl)[1,1-biphenyl]-4-yl)methyl]-2-(trifluoromethyl)-4-pyrimidinamine and the pharmaceutically acceptable salts and solvates thereof;
2,6-dimethyl-5-(2-thienylmethyl)-N-[(2'-(1H-tetrazol-5-yl)[1,1-biphenyl]-4-yl)methyl]-4-pyrimidinamine and the pharmaceutically acceptable salts and solvates thereof;
[2,6-dimethyl-N-[(2'-(1H-tetrazol-5-yl)[1,1-biphenyl]-4-yl)methyl]-4-pyrimidinamin-5-yl]acetic acid and the pharmaceutically acceptable salts and solvates thereof;
2,6-dimethyl-5-(2-propynyl)-N-[(2'-(1H-tetrazol-5-yl)[1,1-biphenyl]-4-yl)methyl]-4-pyrimidinamine and the pharmaceutically acceptable salts and solvates thereof;
6-methyl-5-propyl-N-[[2'-(1H-tetrazol-5-yl)[1,1'-biphenyl]-4-yl]methyl]-2-(trifluoromethyl)-4-pyrimidinamine the pharmaceutically acceptable salts and solvates thereof;
6-methyl-5-(1-methylethyl)-N-[[2'-(1H-tetrazol-5-yl)[1,1'-biphenyl]-4-yl]methyl]-2-(trifluoromethyl)-4-pyrimidinamine the pharmaceutically acceptable salts and solvates thereof;
6-ethyl-N-[[2'-(1H-tetrazol-5-yl)[1,1'-biphenyl]-4-yl]methyl]-2-(trifluoromethyl)-4-pyrimidinamine the pharmaceutically acceptable salts and solvates thereof;

2-cyclopropyl-6-(pentafluoroethyl)-N-[[2'-(1H-tetrazol-5-yl)[1,1'-biphenyl]-4-yl]methyl]-4-pyrimidinamine the pharmaceutically acceptable salts and solvates thereof;

6-ethyl-2-methyl-N-[[2'-(1H-tetrazol-5-yl)[1,1'-biphenyl]-4-yl]-methyl]-4-pyrimidinamine the pharmaceutically acceptable salts and solvates thereof;

5-propyl-N-[[2'-(1H-tetrazol-5-yl)[1,1'-biphenyl]-4-yl]methyl]-2-(trifluoromethyl)-4-pyrimidinamine the pharmaceutically acceptable salts and solvates thereof;

6-ethyl-5-(1-methylethyl)-N-[[2'-(1H-tetrazol-5-yl)[1,1'-biphenyl]-4-yl]methyl]-2-(trifluoromethyl)-4-pyrimidinamine the pharmaceutically acceptable salts and solvates thereof;

5-butyl-6-methyl-N-[[2'-(1H-tetrazol-5-yl)[1,1'-biphenyl]-4-yl]-methyl]-2-(trifluoromethyl)-4-pyrimidinamine the pharmaceutically acceptable salts and solvates thereof;

2-methyl-5-[(3-methylphenyl)methyl]-N-[[2'-(1H-tetrazol-5-yl)[1,1'-biphenyl]-4-yl]methyl]-6-(trifluoromethyl)-4-pyrimidinamine the pharmaceutically acceptable salts and solvates thereof;

4'-[[[6-methyl-2-(trifluoromethyl)-4-pyrimidinyl]amino]methyl][1,1'-biphenyl]-2-carboxylic acid the pharmaceutically acceptable salts and solvates thereof;

5-ethyl-2-methyl-N-[[2'-(1H-tetrazol-5-yl)[1,1'-biphenyl]-4-yl]methyl]-6-(pentafluoroethyl)-4-pyrimidinamine sodium salt hydrate;

2,5-dimethyl-N-[[2'-(1H-tetrazol-5-yl)[1,1'-biphenyl]-4-yl]methyl]-6-(trifluoromethyl)-4-pyrimidinamine sodium salt;

6-methyl-5-(phenylmethyl)-N-[[2'-(1H-tetrazol-5-yl)[1,1'-biphenyl]-4-yl]methyl]-2-(trifluoromethyl)-4-pyrimidinamine sodium salt hydrate;

6-ethyl-5-propyl-N-[[2'-(1H-tetrazol-5-yl)[1,1'-biphenyl]-4-yl]methyl]-2-(trifluoromethyl)-4-pyrimidinamine sodium salt hydrate;

2-methyl-6-(pentafluoroethyl)-N-[[2'-(1H-tetrazol-5-yl)[1,1'-biphenyl]-4-yl]methyl]-4-pyrimidinamine sodium salt hydrate;

2-methyl-N-[[2'-(1H-tetrazol-5-yl)[1,1'-biphenyl]-4-yl]methyl]-6-(trifluoromethyl)-4-pyrimidinamine hydrate;

4'-[[[2-methyl-6-(pentafluoroethyl)-4-pyrimidinyl]amino]methyl][1,1'-biphenyl]-2-carboxylic acid hemihydrate;

4'-[[[2-methyl-6-(trifluoromethyl)-4-pyrimidinyl]amino]methyl][1,1'-biphenyl]-2-carboxylic acid sesquihydrate.

PROCESS

The compounds of the present invention are prepared according to the general sequence of reactions outlined below:

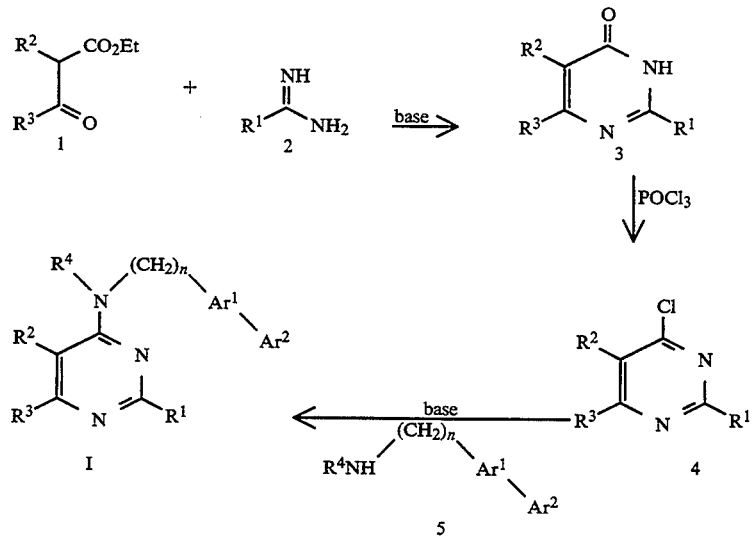

wherein $R^1$, $R^2$, $R^3$, $R^4$, n, $Ar^1$, $Ar^2$ are as defined above.

Thus a β-keto ester 1 is condensed with an amidine 2 in the presence of a base such as sodium ethoxide in an alcoholic solvent such as ethanol at temperatures ranging from ambient to reflux to yield a pyrimidone 3. Treatment of a pyrimidone 3 with phosphorus oxychloride under reflux gives a chloropyrimidine 4. The reaction of 4 with the amine 5 in the presence of an organic base such as triethylamine or an inorganic base such as potassium carbonate in a polar solvent such as ethanol, butanol, or dimethylsulfoxide at temperatures ranging from ambient to reflux yields the target pyrimidines I.

Compounds of formula I in which $R^4$ is alkylcarbonyl are made by acylation of the compounds wherein $R^4$ is hydrogen by standard acylation methods.

The compounds of this invention may also form salts with inorganic or organic bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The present invention also provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, $\beta$-blocking agents or ACE inhibitors.

The present invention further provides a compound of the invention for use as an active therapeutic substance. Compounds described in this invention are of particular use in the treatment of hypertension. They can also be used for the treatment of congestive heart-failure. In addition, the compounds of this invention also have therapeutic utility in the treatment of hyperlipidemia, and/or hypercholesterolemia.

The present invention further provides a method of treating hypertension in mammals including man, which comprises administering to the afflicted mammal an antihypertensive effective amount of a compound or a pharmaceutical composition of the invention.

The high affinity of the compounds for the angiotensin II receptor was established using a rat adrenal receptor binding assay, measuring the displacement of radiolabeled angiotensin II from the receptor, described as follows: Anesthetize male Sprague-Dawley rats (300–400 g body weight) with $CO_2$ and sacrifice by cervical dislocation. Dissect adrenal glands and keep in ice-cold sucrose buffer. (0.2M sucrose, 1 mM EDTA, 10 mM Trizma base, pH=7.2). Remove medulla by squashing. Mince the cortex, rinse and homogenize in a chilled ground glass tissue grinder with 15 ml sucrose buffer. Centrifuge at 3000× g for 10 min. (Sorvall RCSC centrifuge, SS34 rotor 6200 rpm). Decant supernatant through gauze. Centrifuge combined supernatants at 12,000× g for 13 min. (Beckman ultracentrifuge, 80Ti rotor, 13,000 rpm). Centrifuge the supernatant from the previous step at 102,000× g for 60 min. (Beckman ultracentrifuge, 80Ti rotor, 38,200 rpm). All steps are carried out at 4° C. Resuspend the pellet in 0.5 mL assay buffer (50 mM Tris HCl, 5 mM $MgCl_2$, 0.2% BSA (protease-free), pH=7.4, 25° C.). Store on ice. Determine membrane protein by Lowry or Bradford assay with BSA as standard. The binding assay is performed in triplicate, in 12×75 mm plastic test tubes or in 96-well plate (final volume of 0.25 mL). Add 140 $\mu$L assay buffer. Add 10 $\mu$L cold A II (to give final concentrations of $10^{-10}$–$10^{-7}$M for standard curve and $10^{-4}$M for nonspecific binding), compounds (e.g., for final concentrations of 25 and 100 $\mu$M or 1 $\mu$M, 10 nM and 100 nM) in 50% DMSO, or 50% DMSO as a control. Add 50 $\mu$L membrane suspension (e.g., 10 $\mu$g protein). Preincubate for 30 min at 25° C. Add 50 $\mu$l $^{125}$I-A II which has been prepared as shown below (final concentration=1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes 3× with 5 mL cold buffer (assay buffer without BSA). Cut and deposit the filter discs into test tubes and count on gamma counter for 1 min. Adjust the specific activity of $^{125}$I-A II purchased from New England Nuclear to 500 $\mu$Ci/nmole by adding cold A II in water. Calculate the quantities of hot A II and the cold A II needed and make the dilution. Aliquot, seal tight, and store frozen until needed. Calculate the concentration of the total A II (hot+cold) after dilution. On the day of assay, thaw the frozen aliquot and adjust the volume to give a concentration of 5 pmole/mL (or 0.25 pmole/50 $\mu$L) with assay buffer (+protease-free BSA). For final concentration of 1 nM $^{125}$I-A II in the assay, add 50 $\mu$L (or 0.25 pmole) per test tube to a final volume of 250 $\mu$L. The results of these binding assays are reported as the inhibitory concentration of the test compound necessary to achieve fifty percent displacement of radiolabeled angiotensin II from its receptor ($IC_{50}$), or the percent displacement of binding of A II at its receptor at $10^{-8}$M concentration of test compound (% I). All the examples cited in this invention displayed significant inhibition of A II binding in this assay. Typically these compounds displayed an $IC_{50}$ in this assay of less than or equal to 50 $\mu$M.

In accordance with their ability to antagonize angiotensin II, the compounds of this invention show antihypertensive action in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 $\mu$g/kg/min (at 9.6 u Vmin). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the product of Example 47 administered at 3 mg/kg id lowered the A II dependent blood pressure by an average of 57% four hours post-administration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraoccular pressure, and in the enhancement of retinal blood flow. These compounds will also be useful as antidepressants and anxiolytics and in the prevention or treatment of restenosis following angioplasty. The application of the compounds of this invention for these and similar disorders will be apparent to those skilled in the art.

The usefulness of these compounds as lipid lowering agents was assessed using cholesterol absorption in a cholesterol/cholic acid-fed rat model which is described as follows. Newly arrived rats are housed for 5 days in a room with reversed light/dark cycle and fed pelleted rat chow (Purina 5001). The food is removed, and the rats are placed on a daily 4 h/day feeding schedule (beginning at 9:00 AM) with normal chow for 7 days. After acclimation (total of 12 days) and randomization based on weight, dosing with drugs and feeding of cholesterol/cholic acid is initiated. Drug solublized in vehicle (0.1 mL; olive oil, corn oil, 2% Tween 80, or carboxymethyl cellulose) is administered orally through a dosing needle immediately prior to (9:00 AM) and immediately following the 4 h feeding period. Dosing with drugs and feeding of the cholesterol/cholic acid diet is repeated for 4 days. On the morning of the 5th day, rats are sacrificed (decapitation), blood is collected and the livers are removed, weighed and stored frozen ($-80°$ C.). The animals are analyzed for total plasma cholesterol (TPC), high density lipoprotein cholesterol (HDLC, Sigma kit) and triglycerides (TG) on an Abbott Autoanalyzer. VLDL+LDL cholesterol is calculated by the difference between total and HDL cholesterol. HDL cholesterol/total cholesterol is also calculated. Typically the compounds of this invention show a 50% drop in total cholesterol at doses in the range of 100–200 mg/kg.

As illustrated above the compounds of this invention are effective lipid lowering agents and therefore are useful for treating hyperlipidemia and/or hypercholesterolemia.

Specific procedures are described in the following examples. These examples are given to illustrate the invention and should not be construed as limiting the invention set forth in the appended claims.

PHARMACOLOGY

TABLE

| Inhibition of $^{125}$I Angiotensin II Binding | |
|---|---|
| EXAMPLE | IC$_{50}$, nM |
| 34 | 25.0 |
| 35 | 3.0 |
| 36 | 5.6 |
| 37 | 39.0 |
| 38 | 7.8 |
| 39 | 49.0 |

TABLE-continued

| Inhibition of $^{125}$I Angiotensin II Binding | |
|---|---|
| EXAMPLE | IC$_{50}$, nM |
| 40 | 6.5 |
| 41 | 101.0 |
| 42 | 41.0 |
| 43 | 11.0 |
| 44 | 20.0 |
| 45 | 48.0 |
| 46 | 2.5 |
| 47 | 38.0 |
| 48 | 61.0 |
| 50 | 330.0 |
| 51 | 850.0 |
| 52 | 500.0 |
| 53 | 7.5 |
| 54 | 16.0 |
| 55 | 58.0 |
| 56 | 200.0 |
| 57 | 39.0 |

EXAMPLES

Example 1

5-[(4'-Aminomethyl)[1,1-biphen-2-yl]]-1H-tetrazole hydrochloride

The title amine was prepared from 5-[(4'-bromomethyl)[1,1-biphen-2-yl]]-1-triphenylmethyltetrazole (U.S. Pat. Nos. 4,870,186 and 4,874,867 and by J. Duncia et al, J. Org. Chem. (1991) 56 2395–2400) by the "Gabriel amine Synthesis" method, via reaction with potassium phthalimide in DMF at 50° C. for 18 h. The protected amine was treated with hydrazine in refluxing EtOH, followed by treatment with 2N HCl solution to afford the amine hydrochloride as a white solid.

TLC silica gel (CHCl$_3$-MeOH-NH$_4$OH, 7:3:2) R$_f$ 0.20, ninhydrin positive spot.

$^1$H NMR (DMSO-D$_6$) δ 4.00 (d, 2H), 7.10 and 7.40 (q, 4H), 7.45–7.75 (m, 4H).

Example 2

6-Methyl-5-propyl-2-trifluoromethyl-4H-pyrimidin-4-one

Ethyl 2-acetylpentanoic acid (17.2 g, 0.1 mol) in absolute EtOH was treated with 2.3 g, 0.1 mol) sodium until the metal was dissolved. Trifluoroacetamidine (11.5 g, 0.1 mol) was added and the mixture was refluxed for 3 h, then evaporated to dryness. The residue was taken up in H$_2$O, acidified with 2N HCl, and extracted with EtOAc. The organic layer was washed with water (twice), dried, and evaporated to give an oil. Purification by flash chromatography (CH$_2$Cl$_2$, CH$_2$Cl$_2$-EtOAc 5%) afforded 7.5 g (34%) of the desired compound as crystals.

TLC silica gel (CHCl$_3$-MeOH, 25:1) R$_f$0.50.

$^1$H NMR (CDCl$_3$) δ 1.00 (t, 3H), 1.55 (m, 2), 2.60 (t, 2H), 2.42 (s, 3H).

Example 3

6-Methyl-5-(2-propyl)-2-trifluoromethyl-4H-pyrimidin-4-one

Ethyl 2-isopropylacetoacetate (35.8 mL, 0.2 mol) was mixed with trifluoroacetamidine (23 g, 0.2 mol) in MeOH, and then NaOCH$_3$ (21.6 g, 0.4 mol) was added. The mixture was refluxed for 18 h then evaporated to dryness. The residue was taken up in H$_2$O (200 mL) and extracted with ether. The aqueous solution was reduced in volume and acidified with acetic acid to pH 5 then extracted with EtOAc. The combined organic extracts were washed with a small quantity of water, dried over $Na_2SO_4$, then evaporated to afford 28 g of an oil. The crude product was purified by flash chromatography ($CHCl_3$) to provide 16 g (36% yield) of pure compound.

TLC silica gel ($CHCl_3$) $R_f$ 0.45.

$^1H$ NMR ($CDCl_3$) δ 1.32 (d, 6H), 2.43 (s, 3H), 3.11 (m, 1H).

Anal. calcd for $C_9H_{11}F_3N_2O$: C, 49.09; H, 5.04; N, 12.72. Found: C, 49.33; H, 5.08; N, 12.46.

EXAMPLE 4

2-Methyl-6-trifluoromethyl-4H-pyrimidin-4-one

A solution of Na (2.3 g, 0.1 mol) in EtOH (500 mL) was mixed with ethyl 4,4,4-trifluoroacetoacetate (18.4 g, 0.1 mol) and stirred for 15 min. To this solution a mixture of acetamidine hydrochloride (9.45 g, 0.1 mol) in EtOH containing $NaOCH_3$ (5.4 g, 0.1 mol) was added and the rection mixture was refluxed for 25 h. The solvent was evaporated to afford 18 g of a yellow oil. This oil was taken up in $H_2O$, acidified to pH 2 with 2H HCl, and extracted into EtOAc, dried over $Na_2SO_4$ and evaporated to give 8.2 g (46%) of a solid.

TLC silica gel ($CHCl_3$-MeOH, 9:1) $R_f$ 0.4 one spot UV+, $I_2$-.

EXAMPLE 5

2-Methyl-6-pentafluoroethyl-4H-pyrimidin-4-one

A solution of Na (2.3 g, 0.1 mol) in EtOH (125 mL) was mixed with acetamidine hydrochloride (4.72 g, 50 mmol) and the reaction mixture was stirred for 15 min. Ethyl pentafluoropropionylacetate (11.7 g, 50 mmol) was added and the reaction mixture was refluxed for 6 h. The solvent was removed in vacuo, and the residue was taken up in $H_2O$ and acidified with dilute HCl to pH 2. The aqueous solution was extracted with EtOAc and the organic layer was dried over $Na_2SO_4$, then evaporated to afford 6 g of a yellowish solid. The crude product was purified by flash chromatography ($CHCl_3$ containing MeOH 0% to 4%) to provide 2 g (17.5% yield) of a solid.

TLC silica gel ($CHCl_3$-MeOH, 95:5) $R_f$ 0.25 one spot.
$^1H$ NMR ($CDCl_3$) δ 2.58 (s, 3H), 6.78 (s, 1H).

Anal. calcd for $C_7H_5F_5N_2O$: C, 36.86; H, 2.21; N, 12.28. Found: C, 36.97; H, 2.16; N, 12.31.

EXAMPLES 6-17

The following pyrimidones were prepared by a procedure similar to that described in Examples 2-5.

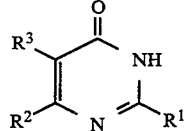

| Example No. | $R^1$ | $R^2$ | $R^3$ |
|---|---|---|---|
| 6 | $CF_3$ | $CH_3$ | H |
| 7 | $CF_3$ | $CH_3$ | $n-C_4H_9$ |
| 8 | $CF_3$ | $C_2H_5$ | H |
| 9 | $CF_3$ | $C_2H_5$ | $n-C_3H_7$ |
| 10 | $CF_3$ | $C_2H_5$ | $iso-C_3H_7$ |
| 11 | $CF_3$ | $CH_3$ | $C_6H_5-CH_2-$ |
| 12 | $CF_3$ | H | $n-C_3H_7$ |
| 13 | $CH_3$ | $C_2H_5$ | H |
| 14 | $CH_3$ | $C_2F_5$ | $C_2H_5$ |
| 15 | $CH_3$ | $CF_3$ | $CH_3$ |
| 16 | $CH_3$ | $CF_3$ | $m-CH_3C_6H_4CH_2-$ |

-continued

| Example No. | $R^1$ | $R^2$ | $R^3$ |
|---|---|---|---|
| 17 | cyclopropyl | $C_2F_5$ | H |

Example 18

4-Chloro-6-methyl-5-(1-butyl)-2-(trifluoromethyl)-pyrimidine

Method A

6-Methyl-5-butyl-2-trifluoromethyl-4H-pyrimidin-4-one of Example 7 (5.00 g, 23 mmol) was mixed with $NaOCH_3$ (1.24 g, 23 mmol) in methanol and evaporated to dryness. The residue was dried by evaporation with benzene, suspended in benzene, and excess phosphorus oxychloride (50 mL) was added. The mixture was refluxed for 2 h then evaporated to a small volume. The residue was poured into crushed ice containing solid $NaHCO_3$ and extracted with EtOAc. The organic layer was washed with water (twice), dried, and evaporated to yield an oil. Purification by flash chromatography ($CHCl_3$) afforded 3.2 g (55%) of an oil. TLC silica gel (cyclohexane-EtOAc, 9:1) $R_f$ 0.50.

Example 19

4-Chloro-6-methyl-5-propyl-2-(trifluoromethyl)pyrimidine

Method B

6-Methyl-5-propyl-2-trifluoromethyl-4H-pyrimidin-4-one of Example 2 (7.0 g, 0.032 mol) was mixed with dimethylaniline (7 mL) and phosphorus oxychloride (35 mL), and the solution was refluxed for 3 h. The cold dark solution was poured into crushed ice containing solid $NaHCO_3$. The mixture was extracted with EtOAc and the organic phase was washed with $H_2O$ (twice), dried, and evaporated to give a dark oil. Purification by flash chromatography ($CHCl_3$) afforded 4.6 g (60%) of the above chloride.

TLC silica gel ($CHCl_3$-MeOH, 25:1) $R_f$ 0.90.

Example 20

4-Chloro-6-methyl-5-(2-propyl)-2-(trifluoromethyl)-pyrimidine

6-Methyl-5-(2-propyl)-2-trifluoromethyl-4H-pyrimidin-4-one of Example 3 (1.66 g, 7.5 mmol) was converted to a Na salt with $NaOCH_3$ then refluxed with phosphorus oxychloride (6 mL) for 3 h. The reaction mixture was concentrated to a small volume, poured into crushed ice, and extracted with $Et_2O$. The organic layer was washed with $H_2O$ (twice), dried over $Na_2SO_4$, and evaporated to give 1.05 g (58%) of a light yellow oil.

TLC silica gel (hexane-EtOAc, 9:1) $R_f$ 0.58.

4-Chloro-2-methyl-6-(trifluoromethyl)pyrimidine

2-Methyl-6-trifluoromethyl-4H-pyrimidin-4-one of Example 4 (2.00 g, 11.2 mmol) was mixed with phosphorus oxychloride (10 mL) and N,N-dimethylaniline (2 mL), and refluxed for 3 h. The dark solution was poured into crushed ice and extracted with Et₂O. The organic layer was washed with H₂O (twice), dried over Na₂SO₄, then evaporated to dryness to afford 2.00 g (91%) of an oil.

TLC silica gel (hexane-EtOAc, 9:1) $R_f$ 0.57.

Example 22

4Chloro-2-methyl-6-(pentafluoroethyl)pyrimidine

2-Methyl-6-pentafluoroethyl-4H-pyrimidin-4-one of Example 5 (1.00 g, 4.4 mmol) was mixed with phosphorus oxychloride (5 mL) and N,N-dimethylaniline (1 mL), and the mixture was refluxed for 3 h. The solution was cooled and poured into crushed ice. The mixture was extracted with Et₂O and the organic layer was washed with H₂O (twice), dried over Na₂SO₄, and evaporated to give 1.05 g (97%) of a yellow-green oil.

TLC silica gel (hexane-EtOAc, 9:1) $R_f$ 0.47 UV+, I₂-.

Examples 23–33

The following chloropyrimidines were prepared according to Example 18 (Method A) or Example 19 (Method B) as indicated

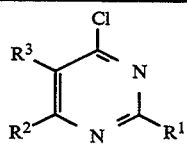

| Example No. | Method | R¹ | R² | R³ |
|---|---|---|---|---|
| 23 | B | CF₃ | CH₃ | H |
| 24 | A | CF₃ | C₂H₅ | H |
| 25 | A | CF₃ | C₂H₅ | n-C₃H₇ |
| 26 | A | CF₃ | C₂H₅ | iso-C₃H₇ |
| 27 | A | CF₃ | CH₃ | C₆H₅CH₂ |
| 28 | B | CF₃ | H | n-C₃H₇ |
| 29 | A | CH₃ | C₂H₅ | H |
| 30 | A | CH₃ | C₂F₅ | C₂H₅ |
| 31 | A | CH₃ | CF₃ | CH₃ |
| 32 | A | CH₃ | CF₃ | m-CH₃C₆H₄CH₂— |
| 33 | A | cyclopropyl | C₂F₅ | H |

Example 34

6-Methyl-5-propyl-N-[[2'-(1H-tetrazol-5-yl)[1,1'-biphenyl]-4-yl]methyl]-2-(trifluoromethyl)-4-pyrimidinamine sodium salt hemihydrate

4-Chloro-6-methyl-5-propyl-2-(trifluoromethyl)-pyrimidine of Example 19 (1.2 g, 5.0 mmol) in n-butanol was mixed with 5-[(4'-aminomethyl)[1,1-biphen-2-yl]]-1H-tetrazole of Example 1 (2.0 g, 7.0 mmol) and sodium acetate (1.0 g, 12.2 mmol) and refluxed for 48 h. The mixture was evaporated to dryness, and the residue was triturated with EtOAc and filtered. The filtrate was evaporated to give 3.0 g of a thick oil. The crude product was purified by flash chromatography (CHCl₃ and CHCl₃-MeOH 2.5%) to afford 460 mg of the desired compound, which was converted to the Na salt with NaOMe in MeOH.

TLC silica gel (CHCl₃-MeOH-NH₄OH, 7:3:2) $R_f$ 0.80.

Anal. calcd for C₂₃H₂₁N₇F₃Na.0.5 H₂O: C, 57.02; H, 4.54; N, 20.24. Found: C, 57.05; H, 5.23; N, 18.15.

Example 35

6-Methyl-5-(1-methylethyl)-N-[[2'-(1H-tetrazol-5-yl)[1,1'-biphenyl]-4-yl]methyl]-2-(trifluoromethyl)-4-pyrimidinamine sodium salt sesquihydrate

4-Chloro-6-methyl-5-(2-propyl)-2-(trifluoromethyl)-pyrimidine of Example 20 (0.44 g, 2.00 mmol) in n-butanol was mixed with the aminotetrazole of Example 1 (0.7 g, 2.2 mmoles) and sodium acetate (1.0 g, 12.2 mmol), and refluxed overnight. The solvent was evaporated to dryness and the residue was taken up in EtOAc (100 mL) and filtered. The filtrate was washed with H₂O, brine, dried over Na₂SO₄, and evaporated to afford 790 mg of gummy material. The crude product was purified by flash chromatography(CHCl₃ containing 5% MeOH) to give 155 mg of a solid. This material was converted to the sodium salt with NaOMe to provide 153 mg (17%) of a solid.

TLC silica gel (CHCl₃-MeOH-1% NH₄OH, 4:1:1) $R_f$ 0.40. ¹H NMR (DMSO-d₆) δ 1.28 (d, 6H), 2.40 (s, 3H), 4.60 (d, 2H), 7–7.20 (q, 4H), 7.25–7.40 (m, 3H), 7.50–7.60 (m, 2H).

Anal. calcd for C₂₃H₂₁F₃N₇Na.1.5 H₂O: C, 54.97; H, 4.82; N, 19.51. Found: C, 55.34; H, 4.72; N, 18.45.

Example 36

6-Ethyl-N-[[2'-(1H-tetrazol-5-yl)[1,1'-biphenyl]-4-yl]methyl]-2-(trifluoromethyl)-4-pyrimidinamine sodium salt sesquihydrate

The title compound was prepared from the chloropyrimidine of Example 24 and the amine of Example 1 in a manner similar to that described in Example 34.

TLC silica gel (CHCl₃-MeOH-NH₄OH, 7:3:2) $R_f$ 0.50.

¹H NMR (DMSO-d₆) δ 1.15 (t, 3H), 2.55 (q, 2H), 4.50 (d, 2H), 6.52 (s, 1H), 7–7.20 (q, 4H), 7.25–7.40 (m, 3H), 7.54 (d, 1H). 8.32 (m, 1H).

Anal. calcd for C₂₁H₁₇N₇F₃Na.1.5 H₂0: C, 53.16; H, 4.22; N, 20.25. Found: C, 53.78; H, 4.06; N, 20.35.

Example 37

2-Cyclopropyl-6-(pentafluoroethyl)-N-[[2'-(1H-tetrazol-5-yl)[1,1'-biphenyl]-4-yl]methyl]-4-pyrimidinamine hydrate

The title compound was prepared from the chloropyrimidine of Example 33 and the amine of Example 1 in a manner similar to that of Example 34.

TLC silica gel (CHCl₃-MeOH-NH₄OH, 7:3:2) $R_f$ 0.80.

¹H NMR (DMSO-d₆) δ 0.90 (d, 4H), 1.98 (m, 1H), 4.50 (d, 2H), 6.71 (s, 1H), 7–7.60 (m, 8H), 8.35 (1H).

Anal. calcd for C₂₃H₁₈N₇F₅.H₂O: C, 54.65; H, 3.96. Found: C, 53.90; H, 4.06.

Example 38

6-Ethyl-2-methyl-N-[[2'-(1H-tetrazol-5-yl)[1,1'-biphenyl]-4-yl]methyl]-4-pyrimidinamine acetate trihydrate

The title compound was prepared from the chloropyrimidine of Example 29 and the amine from Example 1 in a fashion similar to that of Example 34.

TLC silica gel (CHCl₃-MeOH-NH₄OH, 3:1:1) $R_f$ 0.36.

¹H NMR (DMSO-d₆) δ 1.10 (t, 3H), 2.31 (s, 3H), 2.45 (q, 2H), 4.55 (m, 2H), 6.20 (s, 1H), 7–8 (m, 9H).

Example 39

5-Propyl-N-[[2'-(1H-tetrazol-5-yl)[1,1'-biphenyl]-4-yl]methyl]-2-(trifluoromethyl)-4-pyrimidinamine sodium salt hydrate The title compound was prepared from the chloropyrimidine of Example 28 and the amine of Example 1 in a manner similar to that of Example 34.

TLC silica gel (CHCl$_3$-MeOH-NH$_4$OH, 7:3:2) R$_f$ 0.55.

$^1$H NMR (DMSO-d$_6$) δ 0.95 (t, 3H), 1.55 (q, 2H), 2.45 (t, 2H), 4.61 (d, 2H), 7–7.60 (m, 8H), 8.00 (s, 2H).

Anal. calcd for C$_{22}$H$_{19}$N$_7$F$_3$Na.H$_2$O: C, 55.11; H, 4.38. Found: C, 55.25; H, 4.84.

Example 40

6-Ethyl-5-(1-methylethyl)-N-[[2'-1H-tetrazol-5-yl)[1,1'-biphenyl]-4-yl]methyl]-2-(trifluoromethyl)-4-pyrimidinamine sodium salt The title compound was prepared from the chloropyrimidine of Example 26 and the amine of Example 1 in the same manner as described in Example 34.

TLC silica gel (CHCl$_3$-MeOH-NH$_4$OH, 4:1:1) R$_f$ 0.26.

$^1$H NMR (DMSO-d$_6$) δ 1.13 (t, 3H), 1.29 (d, 6H), 2.65 (q, 2H), 3.30 (m, 1H), 4.60 (d, 2H), 6.95–7.60 (m, 8H).

Anal. calcd for C$_{24}$H$_{23}$F$_3$N$_7$Na: C, 58.89; H, 4.74; N, 20.03. Found: C, 58.35; H, 5.06; N, 19.00.

Example 41

5-Butyl-6-methyl-N-[[2'-(1H-tetrazol-5-yl)[1,1'-biphenyl]-4-yl]methyl]-2-(trifluoromethyl)-4-pyrimidinamine sodium salt hydrate The title compound was prepared from the chloropyrimidine of Example 18 and the amine of Example 1 in the same manner as described in Example 34.

TLC silica gel (CHCl$_3$-MeOH-NH$_4$OH, 4:1:1) R$_f$ 0.25.

$^1$H NMR (DMSO-d$_6$) δ 0.90 (m, 3H), 1.40 (m, 4H), 2.33 (s, 3H), 2.53 (m, 2H), 4.56 (d, 2H), 7.00–8.00 (m, 8H).

Anal. calcd for C$_{24}$H$_{22}$F$_3$N$_7$Na.H$_2$O: C, 56.91; H, 4.74; N, 19.36. Found: C, 57.39; H, 5.01; N, 18.75.

Example 42

2-Methyl-5-[(3-methylphenyl)methyl]-N-[[2'-(1H-tetrazol-5-yl)[1,1'-biphenyl]-4-yl]methyl]-6-(trifluoromethyl)-4-pyrimidinamine sodium salt The title compound was prepared from the chloropyrimidine of Example 32 and the amine of Example 1 in the same manner as described in Example 34.

TLC silica gel (CHCl$_3$-MeOH-NH$_4$OH, 7:3:2) R$_f$ 0.60.

$^1$H NMR (DMSO-d$_6$) δ 2.21 (s, 3H), 2.40 (s, 3H), 4.00 (s, 2H), 4.60 (d, 2H), 6.80–7.75 (m, 12H).

Anal. calcd for C$_{28}$H$_{23}$N$_7$F$_3$Na: C, 62.57; H, 4.31. Found: C, 62.38; H, 4.99.

Example 43

5-Ethyl-2-methyl-N-[[2'-(1H-tetrazol-5-yl)[1,1'-biphenyl]-4-yl]methyl]-6-(pentafluoroethyl)-4-pyrimidinamine sodium salt hydrate The chloropyrimidine of Example 30 (2.0 g, 7.3 mmol) was mixed with the amine of Example 1 (2.8 g, 9.7 mmol) and sodium acetate (1.0 g, 12.2 mmol) in n-butanol, and the mixture was refluxed for 6 h. The mixture was evaporated to dryness and the residue was suspended in CHCl$_3$, and filtered. Purification by flash chromatography (CHCl$_3$ and CHCl$_3$-5% MeOH) afforded 0.75 g (21%) of the desired compound.

TLC silica gel 254F (CHCl$_3$-MeOH-NH$_4$OH, 7:3:2) R$_f$0.75 one spot. 440 mg of the above compound were converted to the Na salt with 48.6 mg of NaOMe in MeOH.

TLC system as above R$_f$0.74.

$^1$H NMR (DMSO-d$_6$) δ 1.1 (t, 3H), 2.35 (s, 3H), 2.65 (q, 2H), 4.65 (d, 2H), 7–7.72 (q, 4H), 7.25–7.40 (m, 2H).

Anal. calcd for C$_{23}$H$_{19}$F$_5$N$_7$Na.H$_2$O: C, 52.17; H, 3.96; N, 18.52. Found: C, 51.90; H, 4.26; N, 17.25.

Example 44

2,5-Dimethyl-N-[[2'-(1H-tetrazol-5-yl)[1,1'-biphenyl]-4-yl]methyl]-6-(trifluoromethyl)-4-pyrimidinamine hemihydrate The chloropyrimidine of Example 31 (630 mg, 3.0 mmol) was mixed with the amine of the example 1 (1.1 g, 3.8 mmoles) and sodium acetate (1.5 g, 18.3 mmol) in n-butanol, and the mixture was refluxed for 10 h. The reaction mixture was evaporated to dryness and the residue was suspended in CHCl$_3$. The crude product was purified by flash chromatography (CHCl$_3$ then with CHCl$_3$-MeOH 5%) to afford 610 mg (50%) of a solid. 300 mg of the above solid was mixed with 36 mg of NaOMe in MeOH and evaporated to dryness. Trituration with Et$_2$O and filtration provided the title compound.

TLC silica gel 254F (CHCl$_3$-MeOH-NH$_4$OH, 7:3:2) R$_f$0.75.

$^1$H NMR (DMSO-d$_6$) δ 2.15 (s, 3H), 2.35 (s, 3H), 4.65 (d, 2H), 7.05 (d, 2H), 7.52 (d, 2H), 7.55–7.70 (m, 4H), 7.85 (t, 1H).

Anal. calcd for C$_{21}$H$_{18}$N$_7$F$_3$.0.5H$_2$O: C, 58.06; H, 4.37; N, 22.58. Found: C, 58.11; H, 4.47; N, 22.26.

Example 45

6-Methyl-5-(phenylmethyl)-N-[[2'-(1H-tetrazol-5-yl)[1,1'-biphenyl]-4-yl]methyl]-2-(trifluoromethyl)-4-pyrimidinamine sodium salt hydrate The chloropyrimidine of Example 27 (0.57 g, 2.00 mmole) was mixed with the amine of Example 1 (0.75 g, 2.20 mmol) and sodium acetate (1.0 g, 12.2 mmol) in n-butanol and refluxed overnight. The solvent was removed in vacuo and the residue was taken up in EtOAc and filtered. The filtrate was washed with water and brine, dried over Na$_2$SO$_4$, and evaporated to give 0.97 g of crude product. Purification by flash chromatography (CHCl$_3$ and CHCl$_3$ containing 3%, and 6% MeOH) afforded 272 mg of the pure compound. The above material was converted to the title sodium salt with NaOMe in MeOH to provide 150 mg of a solid.

TLC silica gel (CHCl$_3$-MeOH-NH$_4$OH, 4:1:1) R$_f$0.45.

$^1$H NMR (DMSO-d$_6$) δ 2.27 (s, 3H), 4.00 (s, 2H), 3.15 (d, 2H), 6.95–7.50 (m, 13H), 7.95 (6, 1H).

Example 46

6-Ethyl-5-propyl-N-[[2'-(1H-tetrazol-5-yl)[1,1'-biphenyl]-4-yl]methyl]-2-(trifluoromethyl)-4-pyrimidinamine sodium salt The chloropyrimidine of Example 25 (0.76 g, 3 mmol) was mixed with the aminie of Example 1 (1.0 g, 3.1 mmol) and sodium acetate (1.1 g, 13.3 mmol) in n-butanol and refluxed overnight. The reaction mixture was evaporated to dryness and the residue was purified by flash chromatography (CHCl$_3$ and CHCl$_3$ containing 5% and 7.5% MeOH) to give 290 mg of a solid which was converted to the title compound with NaOMe.

TLC silica gel (CHCl$_3$-MeOH-NH$_4$OH, 7:3:2) R$_f$0.75.

$^1$H NMR (DMSO-d$_6$) δ 1.0 (t, 3H), 1.15 (t, 3H), 1.42 (q, 2H), 2.61 (q, 2H), 4.98 (d, 2H), 7-7.2 (q, 4H), 7.25-7.40 (m, 3H), 7.45 (t, 1H), 7.84 (t, 1H).

Anal. calcd for C$_{24}$H$_{23}$F$_3$N$_7$Na: C, 58.89; H, 4.74. Found: C, 58.56; H, 5.17.

Example 47

2-Methyl-6-(pentafluoroethyl)-N-[[2'-(1H-tetrazol-5-yl)[1,1'-biphenyl]-4-yl]methyl]-4-pyrimidinamine sodium salt hydrate The chloropyrimidine of Example 22 (1.0 g, 4.0 mmol) was mixed with the amine of Example 1 (1.4 g., 4.0 mmoles) and sodium acetate (1.6 g, 20 mmol) in n-butanol and refluxed for 18 h. The solvent was evaporated to dryness and the residue was extracted with ethyl acetate. The organic extract was evaporated to give 1.7 g of a yellow oil. This oil was purified by flash chromatography (CHCl$_3$ and CHCl$_3$ with an increasing concentration of MeOH up to 5%) to give 650 mg (35%) of a solid. TLC silica gel (CHCl$_3$-MeOH-NH$_4$OH, 4:1:1) R$_f$0.36 one spot. 350 mg of the above compound were mixed with 39.2 mg of NaOMe in MeOH and evaporated to dryness. The residue was triturated with Et$_2$O to provide 300 mg of the sodium salt.

TLC silica gel (CHCl$_3$-MeOH-NH$_4$OH, 4:1:1) R$_f$0.25 one spot, UV +.

$^1$H NMR (DMSO-d$_6$) δ 2.40 (s.3H), 4.55 (d, 2H), 6.78 (s, 1H), 7.07-7.17 (m, 4H), 7.33-7.52 (m, 4H), 8.35 (broad, 1H).

Anal. calcd for C$_{21}$H$_{15}$F$_5$N$_7$Na.H$_2$O: C, 50.30; H, 3.42; N, 19.55. Found: C, 50.07; H, 3.40; N, 18.84.

Example 48

2-Methyl-N-[[2'-(1H-tetrazol-5-yl)[1,1'-biphenyl]-4-yl]methyl]-6-(trifluoromethyl)-4-pyrimidinamine hydrate The chloropyrimidine of Example 21 (0.5 g, 2.5 mmol) was mixed with the amine of Example 1 (0.8 g, 2.5 mmol), sodium acetate (1.02 g, 12.5 mmol), and n-butanol and then refluxed overnight. The reaction mixture was filtered and the solvent was removed in vacuo to give a yellow solid which was taken up in EtOAc. The solution was washed with H$_2$O, brine, dried over Na$_2$SO$_4$, and evaporated to provide 1.05 g of crude product. This material was purified by flash chromatography (CHCl$_3$ and CHCl$_3$ containing 2% and 4% MeOH) to give 78 mg (25%) of the title compound as a solid.

TLC silica gel (CHCl$_3$-MeOH-NH$_4$OH, 4:1:1) R$_f$0.20 one spot.

$^1$H NMR (DMSO-d$_6$) δ 2.40 (s, 3H), 4.60 (d, 2H), 6.75 (s, 1H), 7-7.70 (m, 8H), 8.35 (b, 1H).

Anal. calcd for C$_{20}$H$_{16}$F$_3$N$_7$.H$_2$O: C, 55.93; H, 4.23; N, 22.83. Found: C, 56.32; H, 3.85; N, 22.68.

Example 49

4'-Aminomethyl-1,1'-biphenyl-2-carboxylic acid methyl ester

The title compound was prepared from 4'-bromomethyl-1,1'-biphenyl-2-carboxylic acid methyl ester (described in U.S. Pat. No. 4,916,129 and EP 0323841) by standard reactions involving displacement of the bromine with sodium azide followed by catalytic reduction.

Example 50

4'-[[[2-Methyl-6-(pentafluoroethyl)-4-pyrimidinyl]amino]methyl][1,1'-biphenyl]-2-carboxylic acid hemihydrate The chloropyrimidine of Example 22 (0.46 g, 1.90 mmol) and the amine of Example 49 (0.52 g, 1.90 mmol) in methanol (25 mL) were mixed with Et$_3$N (0.25 mL) and refluxed for 18 h. The solvent was removed in vacuo and the residue was taken up in EtOAc. The solution was washed with H$_2$O, brine, dried over Na$_2$SO$_4$, and evaporated to provide 0.55 g of crude product. Purification by flash chromatography (CH$_2$Cl$_2$ containing 2% to 4% EtOAc) afforded 225 mg (26%) of product.

TLC silica gel (hexane-EtOAc, 1:1) R$_f$0.65.

$^1$H NMR (CDCl$_3$) δ 2.58 (s, 3H), 3.62 (s, 3H), 4.61 (broad, 2H), 6.5 (s, 1H), 7.3-7.9 (m, 9H).

The methyl ester was refluxed for 18 h in MeOH (10 mL) containing 1N NaOH (5 mL). The mixture was neutralized with 1N HCl (5 mL) and the solvent was evaporated to dryness to give a light brown solid. Crystallization from Et$_2$O-hexane gave 100 mg of product.

TLC silica gel (CHCl$_3$-MeOH, 9:1) R$_f$0.2 one spot.

$^1$H NMR (DMSO-d$_6$) δ 2.40 (s, 3H), 4.63 (d, 2H), 6.82 (s, 1H), 7.3-7.8 (m, 9H).

Anal. calcd for C$_{21}$H$_{16}$F$_5$N$_3$O$_2$.0.5 H$_2$O: C, 56.50; H, 3.85; N, 9.41. Found: C, 56.37; H, 3.85; N, 9.30.

EXAMPLE 51

4'-[[[2-Methyl-6-(trifluoromethyl)-4-pyrimidinyl]amino]methyl][1,1'-biphenyl]-2-carboxylic acid sesquihydrate 4'-[[[2-Methyl-6-(trifluoromethyl)-4-pyrimidinyl]amino]methyl][1,1'-biphenyl]-2-carboxylic acid methyl ester was prepared from the chloropyrimidine of Example 21 and the amine methyl ester of Example 49 following the procedure described in Example 50.

TLC silica gel (CHCl$_3$-MeOH, 95:5) R$_f$0.48.

$^1$H NMR (CDCl$_3$) δ 2.60 (s, 3H), 3.65 (s, 3H), 4.65 (m, 2H), 6.55 (s, 1H), 7.25-7.90 (m, 9H).

The methyl ester was hydrolized with NaOH solution as in Example 49 to afford the title compound.

TLC silica gel (CHCl$_3$-MeOH, 95:5) R$_f$0.25.

$^1$H NMR (DMSO-d$_6$) δ 2.40 (s, 3H), 4.65 (d, 2H), 6.80 (s, 1H), 7.35-7.5 (m, 8H), 8.50 (t, 1H).

Anal. calcd for C$_{20}$H$_{16}$F$_3$N$_3$O$_2$.1.5 H$_2$O: C, 57.97; H, 4.59; N, 10.14. Found: C, 58.71; H, 4,15; N, 9.36.

Example 52

4'-[[[6-Methyl-2-(trifluoromethyl)-4-pyrimidinyl]amino]methyl][1,1'-biphenyl]-2-carboxylic acid The chloropyrimidine of Example 23 (290 mg, 15 mmol) was mixed with the amine methyl ester of Example 49 (355 mg, 15 mmol) in MeOH and the mixture was refluxed overnight. The solution was evaporated to dryness to provide an oil which was mixed with EtOAc. The solution was filtered and the filtrate was washed with H₂O and brine, dried, and evaporated to afford an oil. Purification by flash chromatography (CHCl₃) gave 167 mg of the desired methyl ester.

TLC silica gel (CHCl₃-MeOH, 95:5) R$_f$0.57.

¹H NMR (CDCl₃) δ 2.40 (s, 3H), 3.68 (s, 3H), 4.60 (b, 2H), 6.30 (s, 1H), 7.25–7.90 (m, 8H).

The methyl ester (150 mg) in MeOH containing 1N NaOH (2.25 mL) was refluxed for 5 h. The solution was neutralized with 1N HCl (2.25 mL) and evaporated to dryness. The residue was triturated with water to afford 85 mg of a white solid.

TLC silica gel (CHCl₃-MeOH, 9:1) R$_f$0.25.

¹H NMR (DMSO-d₆) δ 2.29 (s, 3H), 4.60 (m, 2H), 6.60 (m, 1H), 7.25–7.80 (m, 8H).

Example 53

2,6-Dimethyl-5-(2-propenyl)-N-[(2'-(1H-tetrazol-5-yl)[1,1-biphenyl]-4-yl)methyl]-4-pyrimidinamine Step 1) 2,6-Dimethyl-5-(2-propenyl)-4H-pyrimidin-4-one A mixture of NaOEt (0.118 mol) in EtOH (prepared from 2.7 g of Na in 125 mL of EtOH), acetamidine hydrochloride (5.6 g, 0.059 mol), and ethyl 2-(2-propenyl)acetoacetate (10.0 g, 0.059 mol) was heated under reflux for 22 h. The mixture was concentrated, taken up in water (50 mL), cooled (0° C.), and acidified to pH 4 with conc. HCl. The mixture was extracted with EtOAc, and the extracts were washed with brine, dried (MgSO₄), and concentrated to give an oily white solid. Trituration with ether/hexane gave 2.1 g (22%) of product as a white solid. An analytical sample was recrystallized from ether/hexane, mp 146°–148° C.

¹H NMR (CDCl₃) δ 2.28 (s, 3H), 2.41 (s, 3H), 3.27 (d, J=6.0 Hz, 2H), 5.00 (m, 2H), 5.83 (m, 1H).

Anal. Calcd for C₉H₁₂N₂O: C, 65.83; H, 7.37; N, 17.06. Found: C, 65.81; H, 7.28; N, 17.12.

Step 2) 4-Chloro-2,6-dimethyl-5-(2-propenyl)pyrimidine

A mixture of 2,6-dimethyl-5-(2-propenyl)-4H-pyrimidin-4-one (1.00 g, 6.10 mmol), phosphorus oxychloride (5 mL), and N,N-dimethylaniline (1 mL) was heated under reflux for 3 h. The mixture was concentrated, cooled (0° C.), and ice water was added. The aqueous mixture was neutralized with 2.5N NaOH, extracted with EtOAc, and the extracts were dried (MgSO₄) and concentrated to give a brown oil. Purification by flash chromatography (10% EtOAc/hexane) gave 0.55 g (50%) of product as a yellow oil.

¹H NMR (DMSO-d₆) δ 2.49 (s, 3H), 2.53 (s, 3H), 4.29 (s, 3H), 6.85 (m, 2H), 7.35 (m, 1H).

Step 3) 2,6-Dimethyl-5-(2-propenyl)-N-[(2'-(1H-tetrazol-5-yl)[1,1-biphenyl]-4-yl)methyl]-4-pyrimidinamine A mixture of 4-chloro-2,6-dimethyl-5-(2-propenyl)pyrimidine (1.1 g, 6.02 mmol), 5-[(4'-aminomethyl)[1,1-biphen-2-yl]]-1H-tetrazole hydrochloride (1.73 g, 6.02 mmol), NaOAc (1.48 g, 18.06 mmol), Et₃N (1.83 g, 18.06 mmol), and n-BuOH (20 mL) was heated under reflux for 2 days. The mixture was concentrated, taken up in water, and extracted with EtOAc. The extracts were dried (MgSO₄), concentrated, and triturated with EtOAc/ether to give a yellow solid. Trituration with hot EtOH gave 0.70 g (29%) of product as a yellow solid, mp 259°–260° C.

¹H NMR (DMSO-d₆) δ 2.20 (s, 3H), 2.27 (s, 3H), 3.25 (d, J=5.5 Hz, 2H), 4.60 (d, J=5.8 Hz, 2H), 4.95 (m, 2H), 5.80 (m, 1H), 7.01 (d, J=8.2 Hz, 2H), 7.15 (d, J=8.2 Hz, 2H), 7.45 (d, J=8.7 Hz, 1H), 7.50 (dd, J=8.7, 1.3 Hz, 1H), 7.58 (dd, J=8.7, 1.3 Hz, 1H), 7.61 (d, J=8.7 Hz, 1H), 7.64 (t, J=5.5 Hz, 1H).

Anal. calcd for C₂₃H₂₃N₇: C, 69.50; H, 5.83; N, 24.67. Found: C, 69.49; H, 5.83; N, 24.49.

Example 54

6-Methyl-5-(2-propenyl)-N-[2'-(1H-tetrazol-5-yl)[1,1-biphenyl]-4-yl)methyl]-2-(trifluoromethyl)-4-pyrimidinamine Step 1) 6-Methyl-5-(2-propenyl)-2-(trifluoromethyl)-4H-pyrimidin-4-one A mixture of NaOEt (0.032 mol) in EtOH (prepared from 0.73 g of Na in 35 mL of EtOH), trifluoroacetamidine (5.0 g, 0.045 mol), and ethyl 2-(2-propenyl)acetoacetate (5.4 g, 0.032 mol) was heated under reflux for 22 h. The mixture was concentrated, taken up in water (25 mL), cooled (0° C.), and acidified to pH 4 with conc. HCl. 2.2 g (32%) of product was collected as an off-white precipitate, mp 148°–150° C. An analytical sample was recrystallized from ether/hexane, mp 151°–153° C.

¹H NMR (CDCl₃) δ 2.44 (s, 3H), 3.35 (d, J=6.0 Hz, 2H), 5.02 (m, 2H), 5.83 (m, 1H).

Step 2) 4-Chloro-6-methyl-5-(2-propenyl)-2-(trifluoromethyl)pyrimidine

A mixture of 6-methyl-5-(2-propenyl)-2-(trifluoromethyl)-4H-pyrimidin-4-one (1.00 g, 4.58 mmol) and phosphorous oxychloride (13 mL) was heated under reflux for 4.5 h. The mixture was concentrated, cooled (0° C.), and ice water was added. The mixture was made basic with solid NaOH and extracted with ether. The extracts were washed with brine, dried (MgSO₄), and concentrated to give 0.51 g (48%) of product as a brown oil.

¹H NMR (CDCl₃) δ 2.63 (s, 3H), 3.59 (d, J=6.0 Hz, 2H), 5.00 (d, J=17.1 Hz, 1H), 5.16 (d, J=10.1 Hz, 1H), 5.85 (m, 1H).

Step 3) 6-Methyl-5-(2-propenyl)-N-[(2'-(1H-tetrazol-5-yl)[1,1-biphenyl]-4-yl)methyl]-2-(trifluoromethyl)-4-pyrimidinamine A mixture of 4-chloro-6-methyl-5-(2-propenyl)-2-(trifluoromethyl)pyrimidine (510 mg, 2.16 mmol), 5-[(4'-aminomethyl)[1,1-biphen-2-yl]]-1H-tetrazole hydrochloride (620 mg, 2.16 mmol), NaOAc (530 mg, 6.46 mmol), Et₃N (654 mg, 6.46 mmol), and EtOH (20 mL) was heated under reflux for 2 days. The mixture was concentrated, taken up in water, acidified to pH 4 with 2N HCl, and extracted with EtOAc. The extracts were dried (MgSO₄), concentrated, and purified by flash chromatography (5–25% MeOH/CH₂Cl₂) to give an oily solid. Trituration with ether gave 360 mg (38%) of product as an off-white solid, mp 187°–189° C.

¹H NMR (DMSO-d₆) δ 2.31 (s, 3H), 3.33 (d, J=5.3 Hz, 2H), 4.58 (d, J=5.9 Hz, 2H), 5.01 (m, 2H), 5.83 (m, 1H), 7.01 (d, J=8.2 Hz, 2H), 7.21 (d, J=8.2 Hz, 2H), 7.51 (d, J=7.0 Hz, 1H), 7.55 (d, J=7.5 Hz, 1H), 7.64 (m, 2H), 7.88 (t, J=5.9 Hz, 1H).

Anal. calcd for C₂₃H₂₀F₃N₇: C, 61.19; H, 4.47; N, 21.72. Found: C, 61.38; H, 4.53; N, 21.45.

Example 55

2,6-Dimethyl-5-(2-thienylmethyl)-N-[(2'-(1H-tetrazol-5-yl)[1,1-biphenyl]-4-yl)methyl]-4-pyrimidinamine Step 1) 2,6-Dimethyl-5-(2-thienylmethyl)-4H-pyrimidin-4-one A mixture of NaOEt (0.023 mol) in EtOH (prepared from 0.54 g of Na in 15 mL of EtOH), acetamidine hydrochloride (2.2 g, 0.023 mol), and ethyl 2-acetyl-3-(2-thienyl)propionate (3.5 g, 0.059 mol) was heated under reflux for 18 h. The mixture was concentrated, taken up in water (50 mL), and filtered. The filtrate was cooled (0° C.), acidified to pH 4 with conc. HCl, and 1.2 g (35%) of product was collected by filtration, mp 181°–183° C.

$^1$H NMR (DMSO-d$_6$) δ 2.20 (s, 3H), 2.21 (s, 3H), 3.90 (s, 2H), 6.83 (dd, J=5.3, 1.3 Hz, 1H), 6.90 (dd, J=5.1, 5.3 Hz, 1H), 7.25 (dd, J=5.1, 1.3 Hz, 1H), 12.50 (s, 1H).

Anal. calcd for C$_{11}$H$_{12}$N$_2$OS: C, 59.97; H, 5.49; N, 12.72. Found: C, 59.66; H, 5.39; N, 12.72.

Step 2) 4-Chloro-2,6-dimethyl-5-(2-thienylmethyl)-pyrimidine

A mixture of 2,6-dimethyl-5-(2-thienylmethyl)-4H-pyrimidin-4-one (1.20 g, 5.45 mmol), phosphorus oxychloride (5 mL), and N,N-dimethylaniline (1 mL) was heated under reflux for 2.5 h. The mixture was concentrated, cooled (0° C.), and ice water was added. The aqueous mixture was neutralized with 2.5N NaOH, extracted with EtOAc, and the extracts were dried (MgSO$_4$) and concentrated to give a green oil. Purification by flash chromatography (10% EtOAc/hexane) gave 1.29 g (100%) of product as a brown oil.

$^1$H NMR (DMSO-d$_6$) δ 2.49 (s, 3H), 2.53 (s, 3H), 4.29 (s, 2H), 6.85 (dd, J=5.1, 0.9 Hz, 1H), 6.94 (dd, J=5.1, 5.1 Hz, 1H), 7.36 (dd, J=5.1, 0.9 Hz, 1H).

Step 3) 2,6-Dimethyl-5-(2-thienylmethyl)-N-[(2'-(1H-tetrazol-5-yl)[1,1-biphenyl]-4-yl)methyl]-4-pyrimidinamine A mixture of 4-chloro-2,6-dimethyl-5-(2-thienylmethyl)pyrimidine (1.29 g, 5.45 mmol), 5-[(4'-aminomethyl)[1,1-biphen-2-yl]]-1H-tetrazole hydrochloride (1.56 g, 5.45 mmol), i-Pr$_2$NEt (1.41 g, 10.90 mmol), and n-BuOH (10 mL) was heated under reflux for 2 days. The mixture was concentrated, taken up in water, filtered, and the filtrate was extracted with EtOAc. The extracts were dried (MgSO$_4$), concentrated, and purified by flash chromatography (10% MeOH/CH$_2$Cl$_2$). Trituration with EtOH gave 20 mg (8%) of product as a white solid, mp 262°–263° C.

$^1$H NMR (DMSO-d$_6$) δ 2.26 (s, 3H), 2.28 (s, 3H), 4.09 (s, 2H), 4.60 (d, J=5.8 Hz, 2H), 6.86 (dd, J=5.1, 1.3 Hz, 1H), 6.90 (d, J=8.1 Hz, 2H), 6.92 (dd, J=5.1, 5.1 Hz, 1H), 7.10 (d, J=8.1 Hz, 2H), 7.30 (m, 1H), 7.49 (dd, J=5.1, 1.3 Hz, 1H), 7.51 (dd, J=7.5, 1.2 Hz, 2H), 7.59 (m, 1H), 7.61 (m, 1H), 7.64 (t, J=5.8 Hz, 1H).

Anal. calcd for C$_{25}$H$_{23}$N$_7$S: C, 66.20; H, 5.11; N, 21.62. Found: C, 65.87; H, 5.05; N, 21.38.

Example 56

[2,6-Dimethyl-N-[(2'-(1H-tetrazol-5-yl)[1,1-biphenyl]-4-yl)methyl]-4-pyrimidinamin-5-yl]acetic acid Step 1) Ethyl (2,6-Dimethyl-3H-pyrimidin-4-on-5-yl)acetate A mixture of NaOEt (0.069 mol) in EtOH (prepared from 1.6 g of Na in 100 mL of EtOH), acetamidine hydrochloride (6.5 g, 0.069 mol), and diethyl 2-acetylsuccinate (15.0 g, 0.069 mol) was heated under reflux for 16 h. The mixture was concentrated, taken up in water (50 mL), and acidified with 2N HCl (12 mL). The aqueous mixture was extracted with CH$_2$Cl$_2$, and the extracts were dried (MgSO$_4$) and concentrated. Trituration with ether gave 3.9 g (27%) of product as a white solid, mp 175°–177° C.

$^1$H NMR (DMSO-d$_6$) δ 1.10 (t, 3H), 2.15 (s, 3H), 2.25 (s, 3H), 3.20 (s, 2H), 4.05 (q, 2H), 12.20 (br s, 1H).

Anal. calcd for C$_{10}$H$_{14}$N$_2$O$_3$: C, 57.13; H, 6.71; N, 13.32. Found: C, 57.10; H, 6.63; N, 13.25.

Step 2) Ethyl (4-Chloro-2,6-dimethylpyrimidin-5-yl)acetate

A mixture of ethyl (2,6-dimethyl-3H-pyrimidin-4-on-5-yl)acetate (1.13 g, 5.4 mmol), phosphorus oxychloride (10 mL), and N,N-dimethylaniline (1.3 mL, 10.3 mmol) was heated under reflux for 3.5 h. The reaction mixture was concentrated, poured onto ice, and the resulting mixture was extracted with ether. The combined extracts were washed with water, dried (MgSO$_4$), and concentrated to give 1.2 g (98%) of product as a yellow oil.

$^1$H NMR (DMSO-d$_6$) δ 1.20 (t, 3H), 2.20 (s, 3H), 2.60 (s, 3H), 3.80 (s, 2H), 4.10 (q, 2H).

Step 3) 2,6-Dimethyl-N-[(2'-(1H-tetrazol-5-yl)[1,1-biphenyl]-4-yl)methyl]-4-pyrimidinamin-5-yl]acetic acid A mixture of ethyl (4-chloro-2,6-dimethylpyrimidin-5-yl)acetate (1.0 g, 4.3 mmol), 5-[(4'-aminomethyl)[1,1-biphen-2-yl]]-1H-tetrazole hydrochloride (1.2 g, 4.3 mmol), triethylamine (1.3 mL, 12.9 mmol), sodium acetate (1.1 g, 12.9 mmol), and n-BuOH (20 mL) was heated under reflux for 2 days. The mixture was concentrated and taken up in 1N NaOH (20 mL). After 1 h, the mixture was acidified and the resulting oil was stirred in 25% MeOH/acetone to give a tan solid. Recrystallization from EtOH gave 75 mg (5%) of product, mp 230°–231° C.

$^1$H NMR (DMSO-d$_6$) δ 2.18 (s, 3H), 2.28 (s, 3H), 3.55 (s, 2H) 4.60 (d, J=5.8 Hz, 2H), 6.98 (d, J=8.3 Hz, 2H), 7.18 (d, J=8.3 Hz, 2H), 7.48 (m, 2H), 7.58 (m, 2H), 7.74 (br s, 1H).

Anal. calcd for C$_{22}$H$_{21}$N$_7$O$_2$·0.25H$_2$O: C, 62.92; H, 5.16; N, 23.35. Found: C, 62.88; H, 5.13; N, 22.98.

Example 57

2,6-Dimethyl-5-(2-propynyl)-N-[(2'-(1H-tetrazol-5-yl)[1,1-biphenyl]-4-yl)methyl]-4-pyrimidinamine Step 1) 2,6-Dimethyl-5-(2-propynyl)-4H-pyrimidin-4-one A mixture of NaOEt (0.117 mol) in EtOH (prepared from 2.7 g of Na in 100 mL of EtOH), acetamidine hydrochloride (5.5 g, 0.058 mol), and ethyl 2-(2-propynyl)acetoacetate (8.2 g, 0.049 mol) was heated under reflux for 16 h. The mixture was concentrated, taken up in water (40 mL), cooled (0° C.), and acidified to pH 4 with conc. HCl. The white precipitate (2.24 g, 28%) was collected by filtration. An analytical sample was recrystallized from ether/ethanol, mp 229°–231° C.

$^1$H NMR (DMSO-d$_6$) δ 2.20 (s, 3H), 2.21 (s, 3H), 2.73 (t, J=2.6 Hz, 1H), 3.29 (d, J=2.6 Hz, 2H), 12.4 (br s, 1H).

Anal. calcd for C$_9$H$_{10}$N$_2$O: C, 66.65; H, 6.21; N, 17.27. Found: C, 66.36; H, 6.10; N, 17.02.

Step 2) 4-Chloro-2,6-dimethyl-5-(2-propynyl)pyrimidine

A mixture of 2,6-dimethyl-5-(2-propynyl)-4H-pyrimidin-4-one (2.10 g, 13.0 mmol) and phosphorus oxychloride (50 mL) was heated under reflux for 2.5 h. The mixture was concentrated, cooled (0° C.), and ice water was added. The aqueous mixture was neutralized with solid KOH and 2.1 g (91%) of product was collected by filtration. An analytical sample was recrystallized from ether/hexane, mp 95°–96° C.

$^1$H NMR (DMSO-d$_6$) δ 2.52 (s, 3H), 2.54 (s, 3H), 3.00 (t, J=2.8 Hz, 1H), 3.66 (d, J=2.8 Hz, 2H).

Anal. calcd for C$_9$H$_9$ClN$_2$: C, 59.84; H, 5.02, N, 15.51. Found: C, 59.48; H, 4.97; N, 15.20.

Step 3) 2,6-Dimethyl-5-(2-propynyl)-N-[(2'-(1H-tetrazol-5-yl)[1,1-biphenyl]-4-yl)methyl]-4-pyrimidinamine A mixture of 4-chloro-2,6-dimethyl-5-(2-propynyl)-pyrimidine (0.91 g, 5.04 mmol), 5-[(4'-aminomethyl)[1,1-biphen-2-yl]]-1H-tetrazole hydrochloride (1.45 g, 5.04 mmol), NaOAc (1.24 g, 15.11 mmol), Et$_3$N (1.53 g, 15.11 mmol), and EtOH (20 mL) was heated under reflux for 20 h. The mixture was cooled, acidified to pH 4 with 1N methanolic HCl, and filtered. The filtrate was concentrated and purified by flash chromatography (5–10% MeOH/CH$_2$Cl$_2$) to give an oily yellow solid. The material was taken up in 1N NaOH, filtered to remove a small amount of insoluble material, and the filtrate was extracted with EtOAc (discarded). The filtrate was acidified to pH 4 and the off-white solid was collected by filtration. Trituration with EtOH/ether gave 32 mg (2%) of product, mp 205°–206° C.

$^1$H NMR (DMSO-d$_6$) δ 2.27 (s, 3H), 2.28 (s, 3H), 2.86 (t, J=2.4 Hz, 1H), 3.45 (d, J=2.4 Hz, 2H), 7.01 (d, J=8.1 Hz, 2H), 7.22 (d, J=8.1 Hz, 2H), 7.49 (d, J=7.6 Hz, 1H), 7.53 (d, J=6.5 Hz, 1H), 7.62 (m, 2H).

Anal. calcd for C$_{23}$H$_{21}$N$_7$: C, 69.85; H, 5.35; N, 24.79. Found: C, 69.46; H, 5.79; N, 24.53.

Example 58

3-(3-methylphenyl)-2-(trifluoromethylcarbonyl) propionic acid ethyl ester

Sodium hydride (60% in oil; 8 g, 0.2 mol) in xylenes was cooled in an ice-bath and ethyl 4,4,4-trifluoroacetoacetate (29.3 mL) was added dropwise followed by the α-bromo-m-xylene (27 mL). The mixture was refluxed for 48 h. The solvent was evaporated and the residue was worked up to afford 56 g of an oil.

$^1$H NMR (CDCl$_3$) δ 1.10 (t, 3H), 2.30 (s, 3H), 3.25 (m, 2H), 4.20 (m, 2H), 6.95–7.25 (m, 4H).

What is claimed is:

1. A compound having the formula:

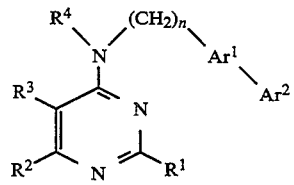

wherein
R$^1$ is alkyl of 1–6 carbon atoms, perfluoroalkyl of 1–6 carbon atoms, cycloalkyl of 3–7 carbon atoms, fluoro, chloro, or bromo;
R$^2$ is hydrogen, alkyl of 1–6 carbon atoms, perfluoroalkyl of 1–6 carbon atoms, trifluoromethylalkyl of 1–6 carbon atoms, cycloalkyl of 3–7 carbon atoms, alkoxy of 1–6 carbon atoms, fluoro, chloro, bromo, or cyano;
R$^3$ is hydrogen, perfluoroalkyl of 1–6 carbon atoms, trifluoromethylalkyl of 1–6 carbon atoms, alkyl of 1–6 carbon atoms, alkenyl of 3–5 carbon atoms, alkynyl of 3–5 carbon atoms, aryl of 6–10 carbon atoms; aryl of 6–10 carbon atoms substituted with fluorine, chlorine or bromine; aralkyl of 7–12 carbon atoms; aralkyl of 7–12 carbon atoms substituted with alkyl of 1–6 carbon atoms, fluorine, chlorine or bromine, alkoxy of 1–6 carbon atoms or alkyl of 1–6 carbon atoms, cycloalkyl of 3–7 carbon atoms, pyridylmethyl, thienylmethyl, fluoro, chloro, bromo, cyano, hydroxyalkyl of 1–6 carbon atoms, (CH$_2$)$_m$CO$_2$R$^5$, (CH$_2$)$_m$CONR$^5$R$^6$;
m is 1 to 4;
n is 0 to 3;
R$^4$ is hydrogen, alkyl of 1–6 carbon atoms, aryl of 6–10 carbon atoms, aryl of 6–10 carbon atoms substituted with halogen, alkylcarbonyl of 1–6 carbon atoms, pyridyl, or pyrimidinyl;
R$^5$ and R$^6$ are H or alkyl of 1–6 carbon atoms;
Ar$^1$ is

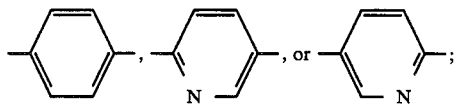

Ar$^2$ is

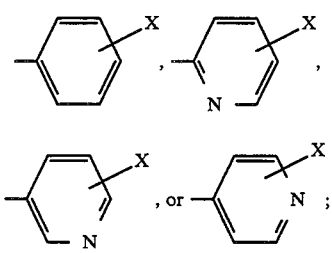

wherein X is CO$_2$H, CO$_2$R$^7$, NHSO$_2$CF$_3$, or

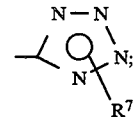

wherein R$^7$ is hydrogen, alkyl of 1–6 carbon atoms, benzyl, triphenylmethyl, or Sn(alkyl of 1–6 carbon atoms)$_3$;
and the pharmaceutically acceptable salts thereof.

2. A compound as claimed in claim 1 having the formula:

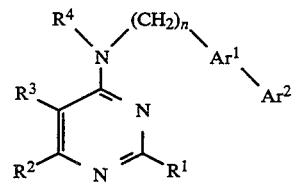

wherein
R$^1$ is alkyl of 1–6 carbon atoms, perfluoroalkyl of 1–6 carbon atoms, or cycloalkyl of 3–7 carbon atoms;
R$^2$ is hydrogen, alkyl of 1–6 carbon atoms, perfluoroalkyl of 1–6 carbon atoms, cycloalkyl of 3–7 carbon atoms, methoxy, chloro, or cyano;
R$^3$ is hydrogen, trifluoromethyl, triflouormethylmethyl, trifluoromethylethyl, alkyl of 1–6 carbon atoms, allyl, alkynyl of 3–5 carbon atoms, phenyl, chlorophenyl, naphthyl, benzyl, benzyl substituted with chlorine or methyl, naphthylmethyl, cyclopropyl, cyclobutyl, cyclopentyl, cyclohexyl, pyridylmethyl, thienylmethyl, chloro, fluoro, cyano, hydroxyalkyl of 1-6 carbon atoms, $(CH_2)_mCO_2R^5$, $(CH_2)_mCONR^5R^6$;

m is 1 to 4;

n is 0 to 3;

$R^4$ is hydrogen, alkyl of 1-6 carbon atoms, phenyl, chlorophenyl, alkylcarbonyl of 1-6 carbon atoms, pyridyl;

$R^5$ and $R^6$ are H or alkyl of 1-6 carbon atoms;

$Ar^1$ is

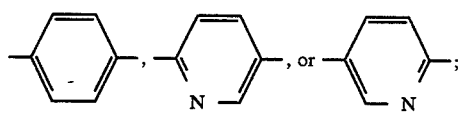

$Ar^2$ is

wherein X is $CO_2H$, $CO_2R^7$, $NHSO_2CF_3$, or

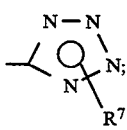

wherein $R^7$ is hydrogen, alkyl of 1-6 carbon atoms, benzyl, triphenylmethyl, or Sn(alkyl of 1-6 carbon atoms)$_3$;

and the pharmaceutically acceptable salts thereof.

3. A compound as claimed in claim 1 having the formula:

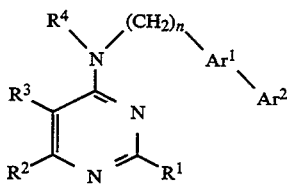

wherein $R^1$ is methyl, ethyl, n-propyl, i-propyl, trifluoromethyl, pentafluoroethyl, cyclopropyl;

$R^2$ is hydrogen, methyl, ethyl, n-propyl, i-propyl, trifluoromethyl, pentafluoroethyl, cyclopropyl;

$R^3$ is hydrogen, methyl, ethyl, n-propyl, i-propyl, n-hexyl, allyl, propargyl, p-chlorophenyl, benzyl, o-chlorobenzyl, 3-methylbenzyl, 2-naphthylmethyl, cyclopropyl, 2-thienylmethyl, hydroxyalkyl of 1-6 carbon atoms, $(CH_2)_mCO_2R^5$;

m is 2;

n is 1;

$R^4$ is hydrogen, acetyl, propionyl;

$R^5$ is H;

$Ar^1$ is

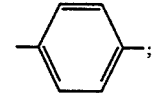

$Ar^2$ is

wherein X is

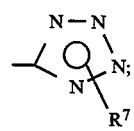

wherein $R^7$ is hydrogen, t-butyl;

and the pharmaceutically acceptable salts thereof.

4. The compound of claim 3, having the name 2,6-dimethyl-5-(2-propenyl)-N-[(2'-(1H-tetrazol-5-yl)[1,1-biphenyl]-4-yl)methyl]-4-pyrimidinamine and the pharmaceutically acceptable salts thereof.

5. The compound of claim 3, having the name 6-methyl-5-(2-propenyl)-N-[(2'-(1H-tetrazol-5-yl)[1,1-biphenyl]-4-yl)methyl]-2-(trifluoromethyl)-4-pyrimidinamine and the pharmaceutically acceptable salts thereof.

6. The compound of claim 3, having the name 2,6-dimethyl-5-(2-thienylmethyl)-N-[(2'-(1H-tetrazol-5-yl)[1,1-biphenyl]-4-yl)methyl]-4-pyrimidinamine and the pharmaceutically acceptable salts thereof.

7. The compound of claim 3, having the name [2,6-dimethyl-N-[(2'-(1H-tetrazol-5-yl)[1,1-biphenyl]-4-yl)methyl]-4-pyrimidinamin-5-yl]acetic acid and the pharmaceutically acceptable salts thereof.

8. The compound of claim 3, having the name 2,6-methyl-5-(2-propynyl)-N-[(2'-(1H-tetrazol-5-yl)[1,1'-biphenyl]-4-yl)methyl]-4-pyrimidinamine and the pharmaceutically acceptable salts thereof.

9. The compound of claim 3, having the name 6-methyl-5--propyl-N-[[2'-(1H-tetrazol-5-yl)[1,1'-biphenyl]-4-yl]methyl]-2-(trifluoromethyl)-4-pyrimidinamine and the pharmaceutically acceptable salts thereof.

10. The compound of claim 3, having the name 6-methyl-5-(1-methylethyl)-N-[[2'-(1H-tetrazol-5-yl)[1,1'-biphenyl]-4-yl]methyl]-2-(trifluoromethyl)-4-pyrimidinamine and the pharmaceutically acceptable salts thereof.

11. The compound of claim 3, having the name 6-ethyl-N-[[2'-(1H-tetrazol-5-yl)[1,1'-biphenyl]-4-yl]methyl]-2-(trifluoromethyl)-4-pyrimidinamine and the pharmaceutically acceptable salts thereof.

12. The compound of claim 3, having the name 2-cyclopropyl-6-(pentafluoroethyl)-N-[[2'-(1H-tetrazol-5-yl)[1,1'-biphenyl]-4-yl]methyl]-4-pyrimidinamine and the pharmaceutically acceptable salts thereof.

13. The compound of claim 3, having the name 6-ethyl-2-methyl-N-[[2'-(1H-tetrazol-5-yl)[1,1'-biphenyl]-4-yl]methyl]-4-pyrimidinamine and the pharmaceutically acceptable salts thereof.

14. The compound of claim 3, having the name 5-propyl-N-[[2'-(1H-tetrazol-5-yl)[1,1'-biphenyl]-4-yl]methyl]-2-(trifluoromethyl)-4-pyrimidinamine and the pharmaceutically acceptable salts thereof.

15. The compound of claim 3, having the name 6-ethyl-5-(1-methylethyl)-N-[[2'-(1H-tetrazol-5-yl)[1,1'-biphenyl]-4-yl]methyl]-2-(trifluoromethyl)-4-pyrimidinamine and the pharmaceutically acceptable salts thereof.

16. The compound of claim 3, having the name 5-butyl-6-methyl-N-[[2'-(1H-tetrazol-5-yl)[1,1'-biphenyl]-4-yl]methyl]-2-(trifluoromethyl)-4-pyridinamine and the pharmaceutically acceptable salts thereof.

17. The compound of claim 3, having the name 2-methyl-5-[(3-methylphenyl)-methyl]-N-[[2'-(1H-tetrazol-5-yl)[1,1'-biphenyl]-4-yl]methyl]-6-(trifluoromethyl)-4-pyrimidinamine and the pharmaceutically acceptable salts thereof.

18. The compound of claim 3, having the name 4'-[[[6-methyl-2-(trifluoromethyl)-4-pyrimidinyl]amino]methyl][1,1'-biphenyl]-2-carboxylic acid and the pharmaceutically acceptable salts thereof.

19. The compound of claim 3, having the name 5-ethyl-2-methyl-N-[[2'-(1H-tetrazol-5-yl)[1,1'-biphenyl]-4-yl]methyl]-6-(pentafluoroethyl)-4-pyrimidin-amine and the pharmaceutically acceptable salts thereof.

20. The compound of claim 3, having the name 2,5-dimethyl-N-[[2'-(1H-tetrazol-5-yl)[1,1'-biphenyl]-4-yl]methyl]-6-trifluoromethyl)-4-pyrimidinamine and the pharmaceutically acceptable salts thereof.

21. The compound of claim 3, having the name 6-methyl-5-(phenylmethyl)-N-[[2'-(1H-tetrazol-5-yl)[1,1'-biphenyl]-4-yl]methyl]-2-(trifluoromethyl)-4-pyrimidinamine and the pharmaceutically acceptable salts thereof.

22. The compound of claim 3, having the name 6-ethyl-5-propyl-N-[[2'-(1H-tetrazol-5-yl)[1,1'-biphenyl]-4-yl]methyl]-2-(trifluoromethyl)-4-pyrimidinamine and the pharmaceutically acceptable salts thereof.

23. The compound of claim 3, having the name 2-methyl-6-(pentafluoroethyl)-N-[[2'-(1H-tetrazol-5-yl)[1,1'-biphenyl]-4-yl]methyl]-4-pyrimidinamine and the pharmaceutically acceptable salts thereof.

24. The compound of claim 3, having the name 2-methyl-N-[[2'-(1H-tetrazol-5-yl)[1,1'-biphenyl]-4-yl]methyl]-6-(trifluromethyl)-4-pyrimidinamine and the pharmaceutically acceptable salts thereof.

25. The compound of claim 3, having the name 4'-[[[2-methyl-6-(pentafluoro-ethyl)-4-pyrimidinyl]amino]methyl][1,1'-biphenyl]-2-carboxylic acid and the pharmaceutically acceptable salts thereof.

26. The compound of claim 3, having the name 4'-[[[2-methyl-6-(trifluoromethyl)-4-pyrimidinyl]amino]methyl][1,1'-biphenyl]-2-carboxylic and the pharmaceutically acceptable salts thereof.

27. A method of treating hypertension in a warm-blooded animal comprising administering to the animal a compound in claim 1 in an amount effective to lower the animal's blood pressure.

* * * * *